United States Patent
Madabhushi et al.

(10) Patent No.: US 11,574,404 B2
(45) Date of Patent: *Feb. 7, 2023

(54) PREDICTING RECURRENCE AND OVERALL SURVIVAL USING RADIOMIC FEATURES CORRELATED WITH PD-L1 EXPRESSION IN EARLY STAGE NON-SMALL CELL LUNG CANCER (ES-NSCLC)

(71) Applicant: Case Western Reserve University, Cleveland, OH (US)

(72) Inventors: Anant Madabhushi, Shaker Heights, OH (US); Pranjal Vaidya, Cleveland, OH (US); Kaustav Bera, Cleveland, OH (US); Prateek Prasanna, Cleveland, OH (US); Vamsidhar Velcheti, Pepper Pike, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 932 days.

This patent is subject to a terminal disclaimer.

(21) Appl. No.: 16/278,325

(22) Filed: Feb. 18, 2019

(65) Prior Publication Data

US 2019/0259156 A1    Aug. 22, 2019

Related U.S. Application Data

(60) Provisional application No. 62/633,377, filed on Feb. 21, 2018.

(51) Int. Cl.
| | |
|---|---|
| *G01N 33/48* | (2006.01) |
| *G06T 7/00* | (2017.01) |
| *G16B 15/00* | (2019.01) |
| *G16B 45/00* | (2019.01) |
| *G16B 40/00* | (2019.01) |

(52) U.S. Cl.
CPC ............ *G06T 7/0014* (2013.01); *G16B 15/00* (2019.02); *G16B 40/00* (2019.02); *G16B 45/00* (2019.02)

(58) Field of Classification Search
None
See application file for complete search history.

(56) References Cited

U.S. PATENT DOCUMENTS

| | | | | |
|---|---|---|---|---|
| 2012/0106821 A1* | 5/2012 | Madabhushi | ........ | G06K 9/6277 382/133 |
| 2013/0202173 A1* | 8/2013 | Buckler | .................. | G06T 7/143 382/131 |

OTHER PUBLICATIONS

Douglas, K. H., et al. "Linear discriminant analysis of regional ejection fractions in the diagnosis of coronary artery disease." European journal of nuclear medicine 12.12 (1987): 602-604.*

Sepesi, Boris, et al. "Programmed death cell ligand 1 (pd-l 1) is associated with survival in stage I non-small cell lung cancer." Seminars in thoracic and cardiovascular surgery. vol. 29. No. 3. WB Saunders, 2017.*

Prasanna, Prateek, Pallavi Tiwari, and Anant Madabhushi. "Co-occurrence of local anisotropic gradient orientations (CoLlAGe): a new radiomics descriptor." Scientific reports 6.1 (2016): 1-14.*

Saeed-Vafa, Daryoush, et al. "Combining radiomics and mathematical modeling to elucidate mechanisms of resistance to immune checkpoint blockade in non-small cell lung cancer." BioRxiv (2017): 190561.*

Zhang, Yucheng, et al. "Radiomics-based prognosis analysis for non-small cell lung cancer." Scientific reports 7.1 (2017): 1-8.*

* cited by examiner

*Primary Examiner* — Anna Skibinsky
(74) *Attorney, Agent, or Firm* — Eschweiler & Potashnik, LLC

(57) ABSTRACT

Embodiments include controlling a processor to perform operations, the operations comprising accessing a digitized image of a region of tissue (ROT) demonstrating cancerous pathology; extracting a set of radiomic features from the digitized image, where the set of radiomic features are positively correlated with programmed death-ligand 1 (PD-L1) expression; providing the set of radiomic features to a machine learning classifier; receiving, from the machine learning classifier, a probability that the region of tissue will experience cancer recurrence, where the machine learning classifier computes the probability based, at least in part, on the set of radiomic features; generating a classification of the region of tissue as likely to experience recurrence or non-recurrence based, at least in part, on the probability; and displaying the classification and at least one of the probability, the set of radiomic features, or the digitized image.

20 Claims, 8 Drawing Sheets

PREDICTING RECURRENCE AND OVERALL SURVIVAL USING RADIOMIC FEATURES CORRELATED WITH PD-L1 EXPRESSION IN EARLY STAGE NON-SMALL CELL LUNG CANCER (ES-NSCLC)

CROSS REFERENCE TO RELATED APPLICATIONS

This application claims the benefit of U.S. Provisional Application 62/633,377 filed Feb. 21, 2018, which is incorporated by reference herein in its entirety.

FEDERAL FUNDING NOTICE

This invention was made with government support under the grant(s) 1U24CA199374-01, R01 CA202752-01A1, R01 CA208236-01A1, R01 CA216579-01A1, and R01 CA220581-01A1, awarded by the National Institutes of Health. Also grant W81XWH-18-1-0440 awarded by the Department of Defense. The government has certain rights in the invention.

BACKGROUND

Outcomes in patients with early stage non-small cell lung cancer (ES-NSCLC) remain poor despite curative intent surgical resection and adjuvant chemotherapy. ES-NSCLC includes stage 1 and stage 2 NSCLC. With increased use of low dose chest computed tomography (CT) screening for lung cancer, there may be an increase in the number of patients diagnosed with ES-NSCLC. Thus, there is a need for clinically validated biomarkers to predict risk of recurrence.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
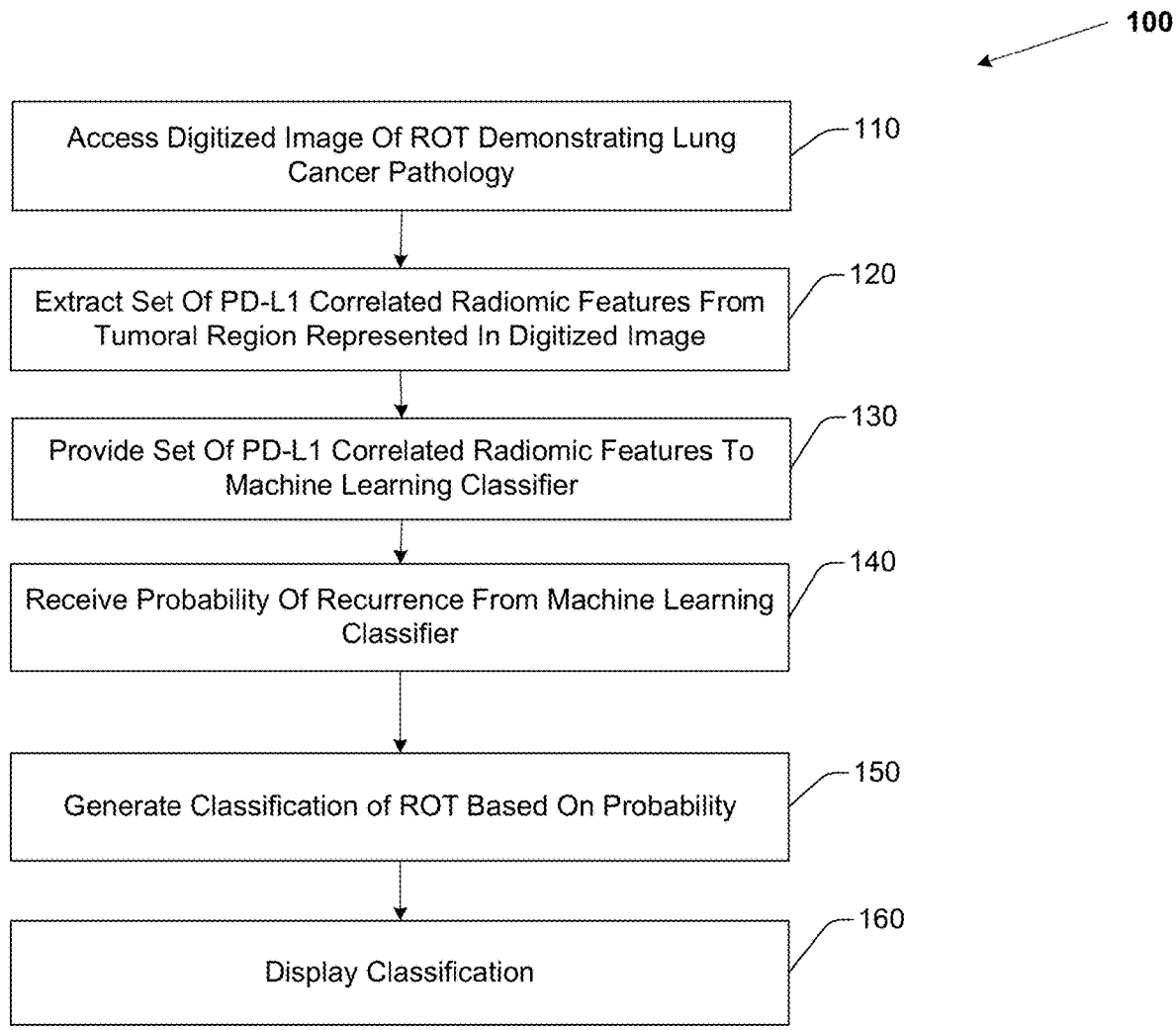
FIG. 1 illustrates operations for predicting recurrence in ES-NSCLC.

Radiomics includes the computerized extraction and analysis of sub-visual attributes for characterizing disease appearance and behavior on radiographic imagery. Radiomic features extracted from pre-surgical CT scans may be used to differentiate between ES-NSCLC patients with high risk of recurrence from those with low risk of recurrence. Embodiments described herein predict risk of recurrence in ES-NSCLC using radiomic features, extracted from pre-surgical CT scans, which are correlated with programmed death-ligand 1 (PD-L1) status. PD-L1 is a transmembrane protein which modulates immune responses in carcinogenesis. Embodiments may further predict overall survival (OS) or disease free survival (DFS) in ES-NSCLC based on the radiomic features.

In one embodiment, a cohort of one-hundred and sixty-six (166) ES-NSCLC patients who had curative surgery with or without adjuvant chemotherapy was chosen for analysis. The recurrence status, OS time, and DFS time for each member of the cohort is known. A set of radiological images of a region of tissue demonstrating ES-NSCLC was acquired of each of the patients, respectively, where a member of the set of radiological images includes a representation of an ES-NSCLC tumor. In this embodiment, a member of the set of radiological images includes a three-dimensional (3D) CT image of a region of tissue demonstrating ES-NSCLC, where a 3D CT image includes a plurality of two-dimensional (2D) slices. In one embodiment, a member of the set of radiological images may have a 2D slice having a slice thickness ranging from 1 mm to 5 mm.

In one embodiment, a tumoral region represented in the member of the set of radiological images is automatically segmented (i.e., annotated) using an automatic or semiautomatic tumor segmentation approach, including for example, a region growing technique. In another embodiment, the tumoral region may be manually segmented by an expert human radiologist using a computerized 3D slicer tool. Segmenting the tumoral region includes defining a tumoral boundary. Radiomic features are extracted from the 2D slices that comprise the tumor volume. In one embodiment, all the 2D slices comprising the tumor region were used for extracting features. In this embodiment, from five to thirty slices per patient were used for feature extraction. In another embodiment, fewer than all the 2D slices that comprise the tumor volume may be employed. For example, the three slices having the largest area per patient may be employed.

Embodiments may evaluate PD-L1 expression in the tumoral regions represented in the set of radiological images. In one embodiment, a set of tissue samples corresponding to the set of radiological images is accessed. PD-L1 expression on the tumor cells in the set of tissue samples is evaluated, in one embodiment, with the E1L3N anti-PDL1 antibody. The human immune system employs a series of checkpoints to protect normal, healthy tissue from an immune response. These checkpoints consist of receptors on the surface of activated T cells and their corresponding ligands on the surface of antigen presenting cells. One such immune checkpoint is triggered when programmed cell death protein 1 (PD-1) engages its ligand PD-L1. As a result of this interaction, T cell activation is attenuated and an active immune response is prevented. This mechanism is often co-opted by tumors. PD-L1 is unregulated in several tumor types and contributes to the malignancy of these cancers by interacting with PD-1 and inhibiting T cell activation. In this way, the tumors avoid detection and destruction by the immune system. Accordingly, PD-1 and PD-L1 may be analyzed for their role in tumor immunology and as immune-based therapeutic targets. Embodiments may detect PD-L1 in tissue samples of the region of tissue represented in the set of radiological images using the PD-L1 antibody EL13N which binds to the PD-L1 protein. In one embodiment, a Western Blot analysis is used to quantify the amount of the antibody-protein bound complex, and indirectly indicate the amount of PD-L1 present in the tumor. In another embodiment, other techniques may be employed to evaluate PD-L1 expression.

In this embodiment, the cohort was divided into a training set (n=116) and an independent validation set (n=50). The training set and the validation set each contain at least one member (i.e., patient) that experienced recurrence, and at least one different member that did not experience recurrence. In another embodiment, other cohort sizes may be employed.

A tumor represented in a member of the set of radiological images has a boundary. Embodiments define a peritumoral region based on a morphological transformation of the tumoral boundary. A peritumoral region may be defined as the region surrounding the tumoral region out to a distance. For example, in one embodiment, the peritumoral region may be the region extending 2 mm from the tumoral boundary. In another embodiment, the peritumoral region may be the region extending 6 mm from the tumoral boundary. The peritumoral region may be defined by a distance measured in mm, as described, or in other units, including pixels.

Figure 8A:
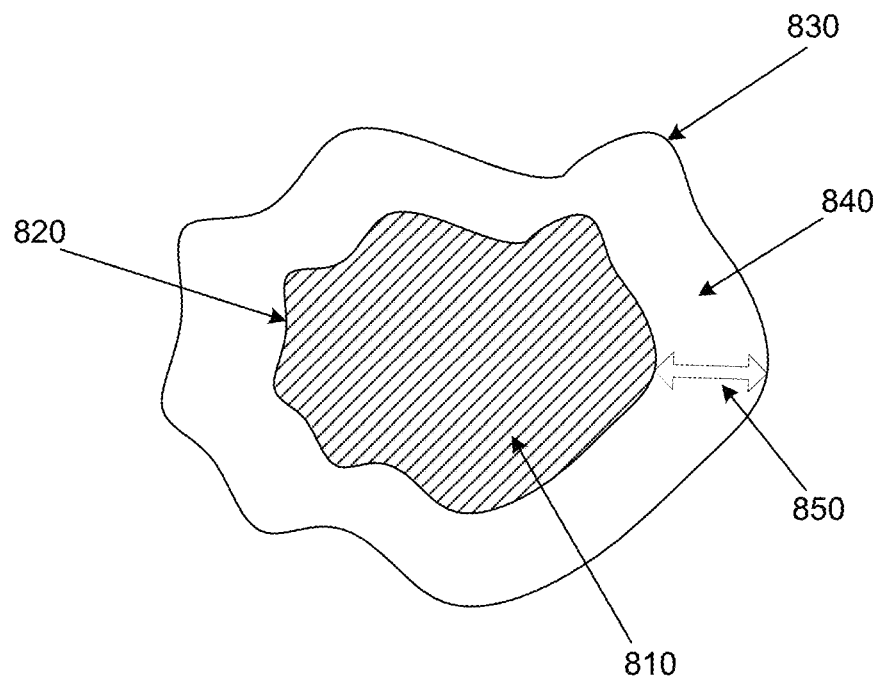
FIGS. 8A-8B illustrate example peritumoral regions.

FIG. 8A illustrates an example peritumoral region 840 associated with an ES-NSCLC tumor 810. Peritumoral region 840 is bounded by outer peritumoral boundary 830 and tumoral boundary 820. In one embodiment, example operations, methods, and apparatus morphologically dilate tumoral boundary 820 by an amount 850, resulting in the outer peritumoral boundary 830. Amount 850 may be, for example, 2 mm, 4 mm, 6 mm, 6 pixels, 8 pixels, or another, different amount.

In another embodiment, the peritumoral boundary may be generated using other techniques. For example, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where the dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary.

Figure 8B:
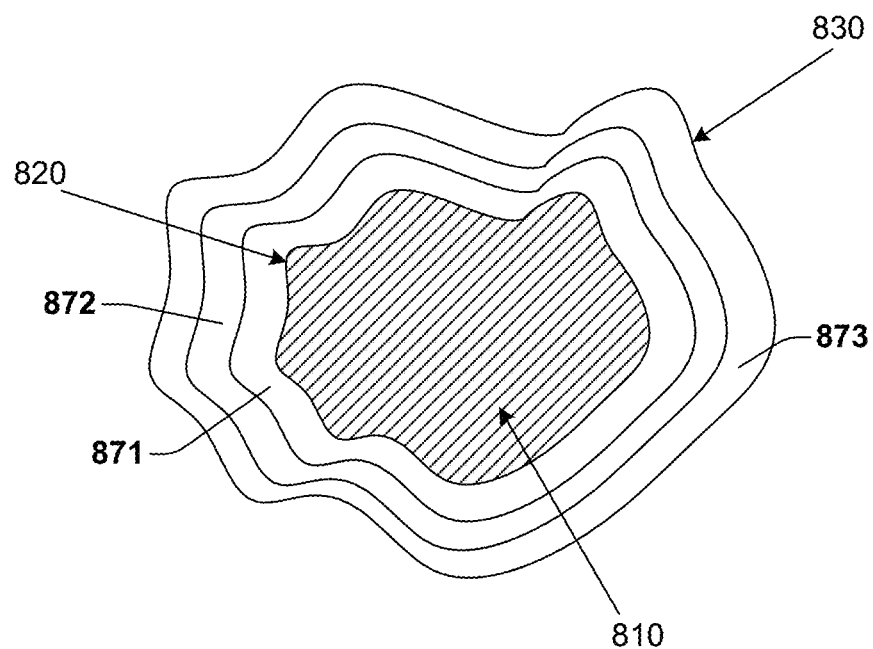

In one embodiment, the peritumoral region is defined using 2 mm annular rings defined about the boundary of the tumoral region out to a radius of 6 mm from the boundary. FIG. 8B illustrates an example peritumoral region that includes three annular rings 871, 872, and 873 defined from the peritumoral boundary 820. Annular ring 871 extends from 0 mm to 2 mm from the tumoral boundary. Annular ring 872 extends from 2 mm to 4 mm from the tumoral boundary. Annular ring 873 extends from 4 mm to 6 mm from the tumoral boundary. In another embodiment, other annular band sizes, radii, numbers of band, or techniques may be employed to define the peritumoral region.

Embodiments select the most discriminative radiomic features in separating presence of PD-L1 expression from its absence. In one embodiment, a total of 248 intratumoral and peritumoral radiomic features were extracted from each member of the set of radiomic images, respectively. In one embodiment, a minimum redundancy, maximum relevance (mRMR) feature selection method is employed to select the most discriminative radiomic features. In another embodiment, a different feature selection approach, including, for example, a Wilcoxon rank sum test (WRST), a t-test, or a Random Forest (RF) feature selection approach may be employed. In one embodiment, the mRMR feature selection approach was employed to select the top three most discriminative features from the 248 radiomic features. The top three features included one intratumoral feature, and two peritumoral features, representing textural heterogeneity inside and outside the tumor (i.e., nodule), respectively. In this embodiment, the intratumoral feature is an intratumoral Laws feature. In this embodiment, the two peritumoral features include a peritumoral Gabor feature (f=2, $\theta=3\pi/8$) extracted from a first peritumoral annular ring (0 mm-2 mm), and a CoLIAGe feature extracted from a third peritumoral annular ring (e.g., annular ring 873, 4 mm-6 mm). CoLIAGe features capture local anisotropic differences in voxel-level gradient orientations to distinguish similar appearing phenotypes. CoLIAGe features involve assigning an image voxel an entropy value associated with the co-occurrence matrix of gradient orientations computed around every voxel in a region of interest. In another embodiment, the peritumoral features may be extracted from other, different annular rings, or the peritumoral region may be defined using other, different dimensions (e.g., different annular ring radii). While in this embodiment three features are selected, in another embodiment, other numbers of features, or different features, may be extracted.

Embodiments may train a machine learning classifier to predict recurrence using the top three most discriminative features. The machine learning classifier may also be trained to compute an OS prognosis or a DFS prognosis. In one embodiment, the machine learning classifier trained on the top three most discriminative features correlated with PD-L1 expression predicts recurrence on the independent validation set (n=50) with an AUC of at least 0.73. The machine learning classifier was also prognostic of OS ($p<0.001$) and DFS ($p<0.001$). In one embodiment, the machine learning classifier is a linear discriminant analysis (LDA) trained using the set of most discriminative radiomic features on a training set of images, and tested on the independent validation set. In another embodiment, the machine learning classifier may be a quadratic discriminant analysis (QDA) classifier, a diagonal linear discriminant analysis (DLDA) classifier, a random forest (RF) classifier, a support vector machine (SVM), or a convolutional neural network (CNN) classifier.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 is a flow diagram of example operations 100 that may be performed by a processor to predict recurrence, including ES-NSCLC recurrence, in a patient demonstrating lung cancer. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 includes, at 110, accessing a digitized image of a region of tissue (ROT) demonstrating cancerous pathology. The image has a plurality of pixels, a pixel having an intensity. In one embodiment, the digitized image is a three dimensional (3D) computed-tomography (CT) image of a region of tissue demonstrating early stage non-small cell lung cancer (ES-NSCLC). In one embodiment, the 3D CT image includes a plurality of two-dimensional (2D) slices having a slice-thickness of between 1 mm and 5 mm respectively, where the set of radiomic features are extracted from at least one of the plurality of 2D slices. While digitized images acquired using CT are described in this example, images acquired using other imaging modalities or having other imaging parameters may be employed. Accessing the digitized image includes acquiring electronic data, reading from a computer file, receiving a computer file, reading from a computer memory, or other computerized activity not practically performed in a human mind.

The set of operations 100 also includes, at 120, extracting a set of radiomic features from the digitized image. The set of radiomic features are positively correlated with PD-L1 expression in tissue demonstrating ES-NSCLC. In one embodiment, the set of radiomic features includes at least two peritumoral features and at least one intratumoral feature. The peritumoral region may include a plurality of annular rings defined from the tumoral boundary. In one embodiment, the at least two peritumoral features are extracted from a peritumoral region extending from 0 mm to 6 mm from a boundary of the tumor represented in the image. In one embodiment, the at least two peritumoral features includes a peritumoral Gabor feature ($f=2$, $\theta=3\pi i/8$) extracted from a first 0 mm to 2 mm peritumoral annular ring, (e.g., annular ring 871) and a CoLlAGe feature extracted from a third 4 mm to 6 mm peritumoral annular ring (e.g., annular ring 873). In one embodiment, the at least one intratumoral feature includes a Laws feature. In another embodiment, other, different radiomic features may be extracted, or other numbers of radiomic features may be extracted. Extracting radiomic features includes acquiring electronic data, reading from a computer file, receiving a computer file, reading from a computer memory, or other computerized activity not practically performed in a human mind.

The set of operations 100 also includes, at 130, providing the set of radiomic features to a machine learning classifier. In one embodiment, the machine learning classifier is an LDA classifier. In another embodiment, other types of machine learning classifiers, including a QDA classifier, a random forest classifier, or a deep learning classifier, including a CNN, may be employed. Providing the set of radiomic features to the machine learning classifier includes acquiring electronic data, reading from a computer file, receiving a computer file, reading from a computer memory, or other computerized activity not practically performed in a human mind.

The set of operations 100 also includes, at 140, receiving, from the machine learning classifier, a probability that the region of tissue will experience cancer recurrence. The machine learning classifier computes the probability based, at least in part, on the set of radiomic features. Receiving, from the machine learning classifier, the probability, includes acquiring electronic data, reading from a computer file, receiving a computer file, reading from a computer memory, or other computerized activity not practically performed in a human mind.

The set of operations 100 also includes, at 150, generating a classification of the region of tissue as likely to experience recurrence or non-recurrence. For example, embodiments may classify the region of tissue as likely to experience recurrence when the probability $>=0.5$, and may classify the region of tissue as unlikely to experience recurrence when the probability $<0.5$. Other classification schemes may be employed. The classification is generated, based, at least in part, on the probability. In one embodiment, the classification is further based on the image. Generating the classification includes acquiring electronic data, reading from a computer file, receiving a computer file, reading from a computer memory, or other computerized activity not practically performed in a human mind.

The set of operations 100 further includes, at 160, displaying the classification and at least one of the probability, the set of radiomic features, or the digitized image. Displaying the classification and at least one of the probability, the set of radiomic features, or the digitized image may include displaying the classification and at least one of the probability, the set of radiomic features, or the digitized image on a computer monitor, a smartphone display, a tablet display, or other displays. Displaying the classification and at least one of the probability, the set of radiomic features, or the digitized image may also include printing the classification and at least one of the probability, the set of radiomic features, or the digitized image. Displaying the classification and at least one of the probability, the set of radiomic features, or the digitized image may also include controlling a recurrence prediction system, a personalized medicine system, a monitor, or other display, to display operating parameters or characteristics of a machine learning classifier, during both training and testing of the machine learning classifier, or during clinical operation of the machine learning classifier. By displaying the classification and at least one of the probability, the set of radiomic features, or the digitized image, example embodiments provide a timely and intuitive way for a human medical practitioner to more accurately classify a region of tissue represented in radiological images as likely to experience recurrence, or unlikely to experience recurrence, thus improving on existing approaches to predicting recurrence. Embodiments may further display operating parameters of the machine learning classifier.

While FIG. 1 illustrates various actions occurring in serial, it is to be appreciated that various actions illustrated in FIG. 1 could occur substantially in parallel. By way of illustration, a first process could involve accessing a CT image, a second process could involve extracting radiomic features from a tumoral region represented in the CT image, and a third process could involve extracting radiomic features from a peri-tumoral region. While three processes are described, it is to be appreciated that a greater or lesser number of processes could be employed and that lightweight processes, regular processes, threads, and other approaches could be employed.

Figure 2:
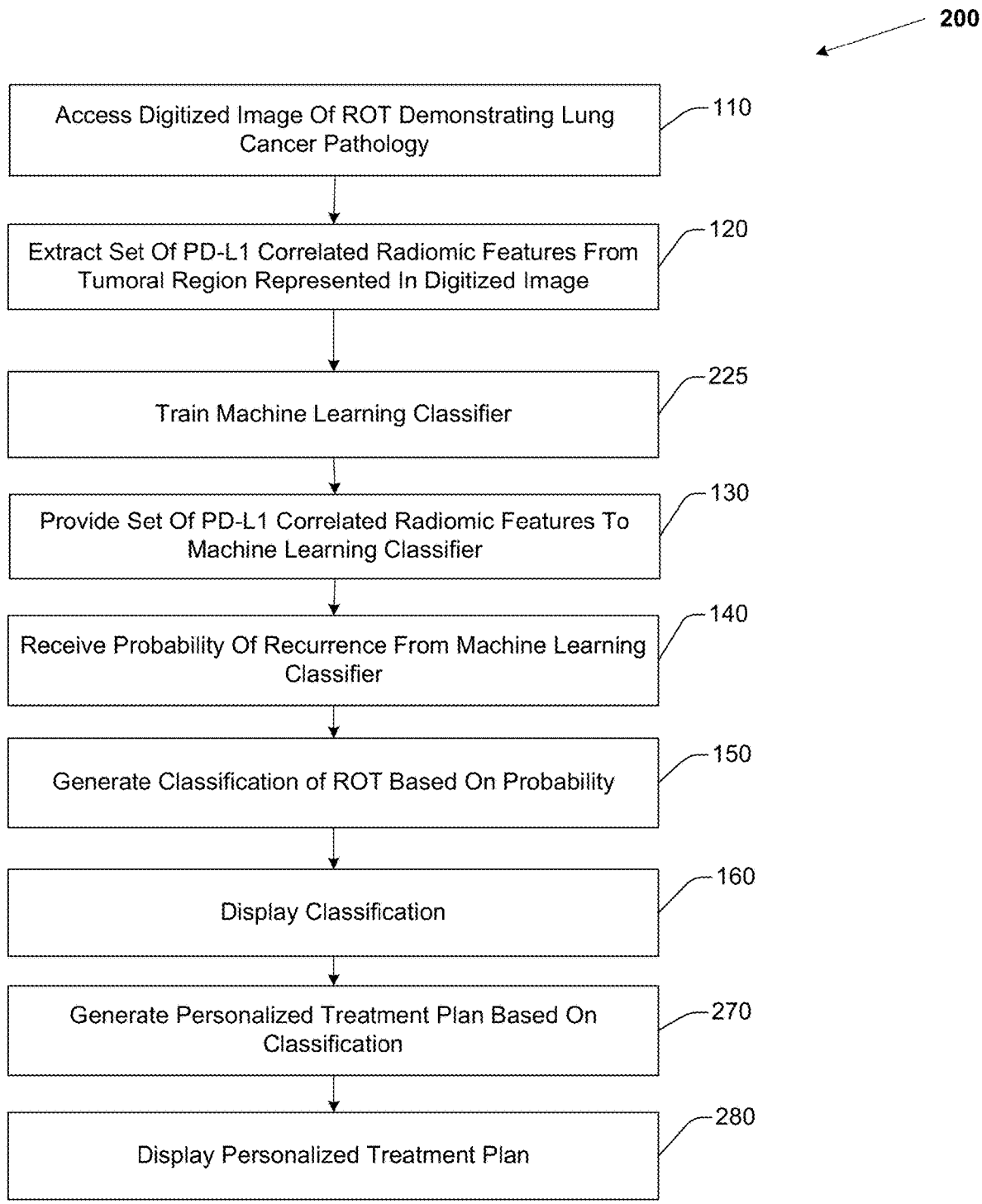
FIG. 2 illustrates operations for predicting recurrence in ES-NSCLC.
Figure 3:
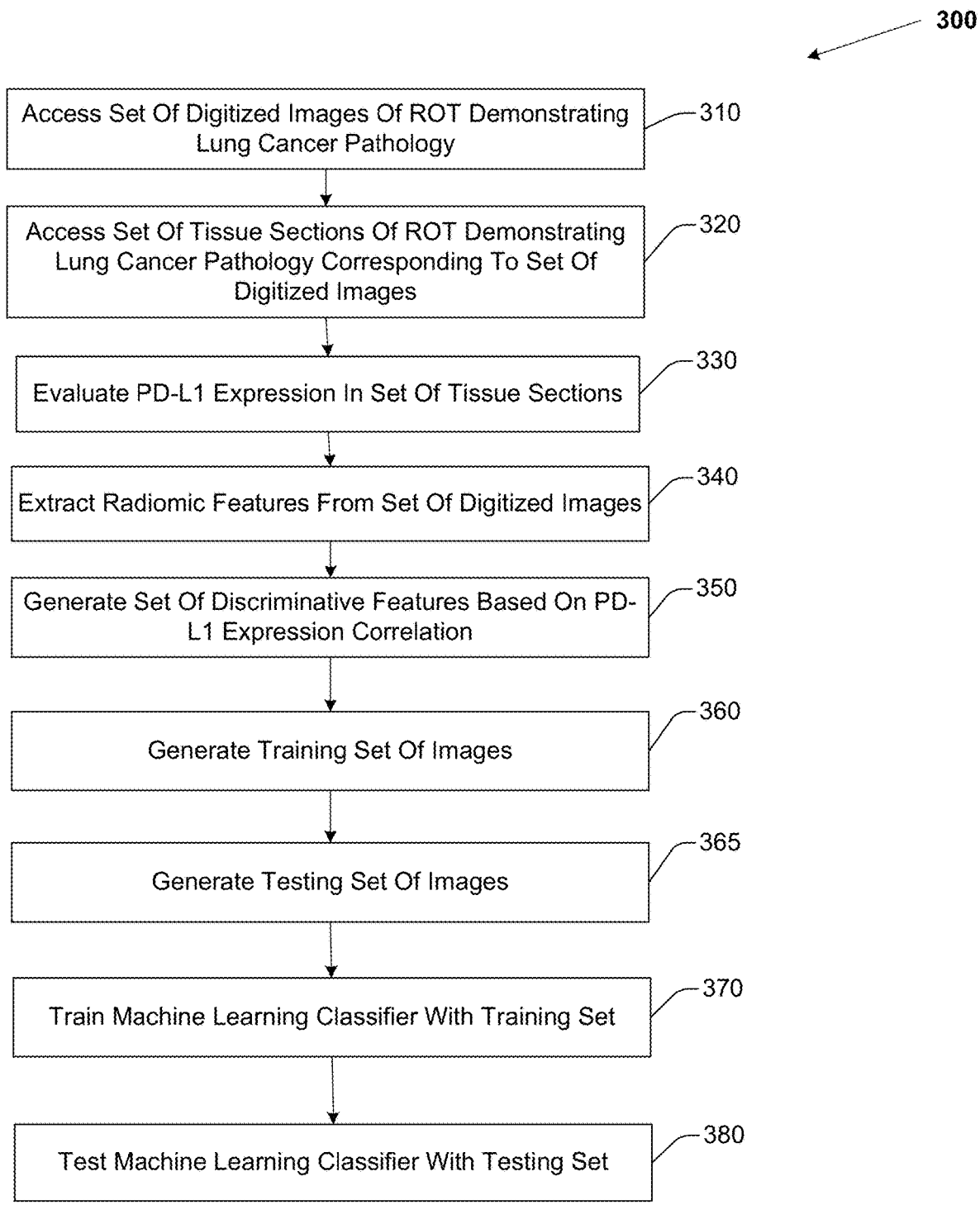
FIG. 3 illustrates operations for training a machine learning classifier to predict recurrence in ES-NSCLC.

FIG. 2 illustrates a set of operations 200 that is similar to operations 100 but that includes additional details and elements. Operations 200 include, at 225, training the machine learning classifier to compute the probability that the region of tissue will experience cancer recurrence. FIG. 3 illustrates operations 300 for training the machine learning classifier. In one embodiment, operations 300 include, at 310, accessing a set of digitized images. A member of the set of digitized images includes a ROT demonstrating cancerous pathology, where a digitized image includes a plurality of pixels, a pixel having an intensity. The ROT represented in a member of the set of digitized images includes a tumoral region, and peritumoral region. The set of digitized images includes images acquired of patients who had curative surgery, with or without adjuvant chemotherapy. A recurrence status, an OS time, and a DFS time for each patient, respectively, are known.

The set of operations 300 also includes, at 320, accessing a set of tissue sections of the ROT corresponding to each member of the set of images, respectively. A member of the set of tissue sections may include, for example, formalin fixed paraffin (FFPE) embedded tissue obtained from surgically resected early stage non-small cell lung cancer patients. The FFPE embedded tissue may be cut into the sections and whole slides created. These whole slides are evaluated, in one embodiment, using PD-L1 antibody EL13N to quantify PD1 or PDL1 status.

The set of operations 300 also includes, at 330, evaluating PD-L1 expression in members of the set of tissue sections. In one embodiment, PD-L1 expression in each of the tissue sections is evaluated. In one embodiment, PD-L1 expression is evaluated using the PD-L1 antibody EL13N which binds to the PD-L1 protein. In this embodiment, a Western Blot analysis is used to quantify the amount of the antibody-protein bound complex. In another embodiment, PD-L1 expression may be evaluated using other techniques. In another embodiment, PD-L1 expression for the tissue sections is already known, and thus, in this embodiment, step 330 may be skipped.

The set of operations 300 also includes, at 340, extracting a set of radiomic features from the set of digitized images. In one embodiment, the set of radiomic features includes 248 radiomic features extracted from tumoral and peritumoral regions of the members of the set of digitized images. In another embodiment, another, different number of radiomic features may be extracted.

The set of operations 300 also includes, at 350, generating a set of discriminative features by selecting a threshold number of the top radiomic features that discriminate PD-L1 expression from absence of PD-L1. In one embodiment, an mRMR feature selection technique is employed to select the top three most discriminative features. In this embodiment, the set of discriminative features includes three features, including one tumoral feature and two peritumoral features. For example, in one embodiment, the two peritumoral features includes a peritumoral Gabor feature ($f=2$, $\theta=3\pi i/8$) extracted from a first 0 mm to 2 mm peritumoral annular ring, and a CoLIAGe feature extracted from a third 4 mm to 6 mm peritumoral annular ring. In this embodiment, the intratumoral feature includes a Laws feature.

The set of operations 300 also includes, at 360, generating a training set of images. The training set is a first subset of the set of images. The training set of images includes at least one image acquired of a patient that experienced recurrence, and at least one image acquired of a patient that did not experience recurrence. In one embodiment, the training set includes imagery acquired of $n=116$ patients.

The set of operations 300 also includes, at 365, generating a testing set of images. The testing set is a second, disjoint subset of the set of images. The testing set includes at least one image acquired of a patient that experienced recurrence, and at least one image acquired of a patient that did not experience recurrence. In one embodiment, the testing set includes imagery acquired of $n=50$ patients.

The set of operations 300 also includes, at 370, training the machine learning classifier to generate a probability of recurrence using the training set. Training the machine learning classifier may include training the machine learning classifier until a threshold level of accuracy is achieved, until a threshold time has been spent training the machine learning classifier, until a threshold amount of computational resources have been expended training the machine learning classifier, until a user terminates training, or some combination thereof. Other training termination conditions may be employed. Once the machine learning classifier has been trained, it can be applied to new imaging data without repeating training, however training may optionally be repeated in order to make adjustments to the machine learning classifier given a new set of training data, for example to improve performance among images acquired with a different type of CT scanner or at a different medical institution.

The set of operations 300 further includes, at 380, testing the machine learning classifier using the testing set. Testing the machine learning classifier may include using an independent validation set which is distinct from the training set used for modeling the classifier. Statistical matrices, including AUC (area under receiver operating curve), accuracy, sensitivity, or precision may be computed to evaluate performance of the machine learning classifier on the validation set based on the outcome of interest (e.g., recurrence vs. non-recurrence).

In one embodiment, the set of operations 300 may also include training the machine learning classifier to generate a prognosis of OS. In another embodiment, the set of operations 300 may also include training the machine learning classifier to generate a prognosis of DFS. The same set of features may be used for predicting OS and DFS. The classifier predicts the prognostic outcome of interest (e.g., OS, DFS) whether the patient had recurrence or not. The classifier's predicted labels may be used to stratify the validation patient population using OS and DFS using Kaplan-Meier survival analysis for early stage lung cancer cases.

Returning to FIG. 200, the set of operations 200 may also include, at 270, generating a personalized cancer treatment plan. The personalized cancer treatment plan may be generated based, at least in part, on the classification and at least one of the probability, the set of radiomic features, or the digitized image. The personalized cancer treatment plan may be generated for the patient of whom the radiological image was acquired based, at least in part, on the classification, the radiological image, or the set of radiomic features. Defining a personalized cancer treatment plan facilitates delivering a particular treatment that will be therapeutically active to the patient, while minimizing negative or adverse effects experienced by the patient. For example, the personalized cancer treatment plan may suggest a surgical treatment, may define an immunotherapy agent dosage or schedule, or a chemotherapy agent dosage or schedule, for a patient identified as likely to experience recurrence. For a patient classified as unlikely to experience recurrence, other treatments may be suggested. Generating the personalized cancer treatment plan includes acquiring electronic data, reading from a computer file, receiving a computer file, reading from a computer memory, or other computerized activity not practically performed in the human mind.

The set of operations 200 may further include, at 280, displaying the personalized cancer treatment plan according to embodiments described herein.

Figure 4:
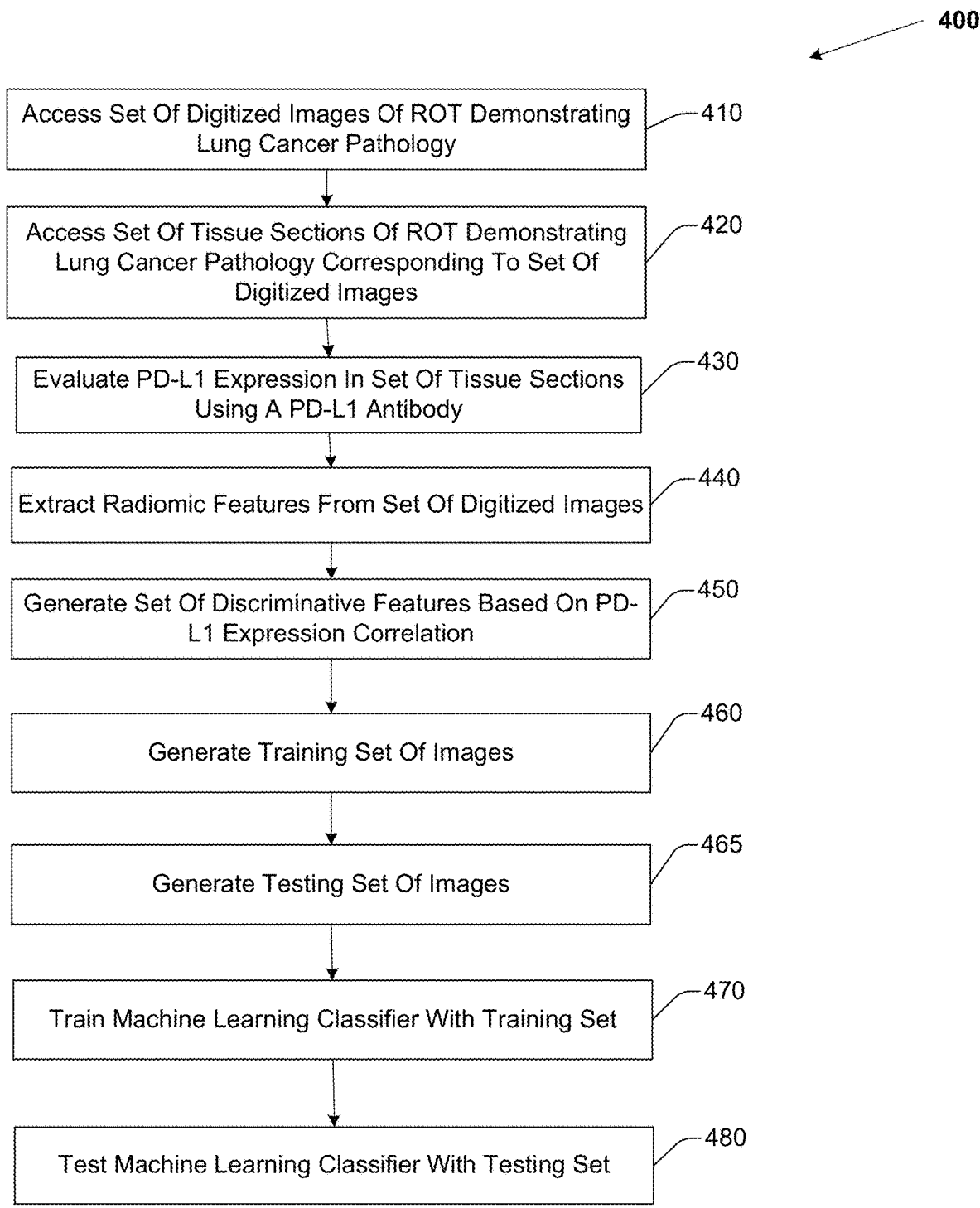
FIG. 4 illustrates an example method for training a machine learning classifier to predict recurrence in ES-NSCLC.

FIG. 4 illustrates a method 400 for training a machine learning classifier to predict ES-NSCLC recurrence. Method 400 includes, at 410, accessing a set of digitized images of a ROT demonstrating ES-NSCLC pathology, where the ROT includes a tumoral region and a peritumoral region. A digitized image includes a plurality of pixels, a pixel having an intensity. The set of digitized images includes images of patients who had curative surgery, with or without adjuvant chemotherapy. A recurrence status, an OS time, and a DFS time for each patient, respectively, is known. Accessing the set of digitized images includes acquiring electronic data, reading from a computer file, receiving a computer file, reading from a computer memory, or other computerized activity not practically performed in the human mind.

Method 400 also includes, at 420, accessing a set of tissue sections of the ROT corresponding to each member of the set of images, respectively. A member of the set of tissue sections may include, for example, formalin fixed paraffin embedded (FFPE) tissue obtained from surgically resected early stage non-small cell lung cancer patients. The FFPE tissue is cut into the sections from which whole slides are created. These whole slides are evaluated using PD-L1 antibody EL13N to quantify PD1 or PDL1 status.

Method 400 also includes, at 430, evaluating PD-L1 expression in each of the tissue sections using a PD-L1 antibody approach. In another embodiment, other techniques may be employed to evaluate PD-L1 expression. In another embodiment, the PD-L1 expression for each tissue section is already known, and thus step 430 may be skipped. In another embodiment, PD-L1 expression may be evaluated in a threshold number of the tissue sections, for example, 75%, or 90% or the tissue sections.

Method 400 also includes, at 440, extracting a set of radiomic features from the set of digitized images. In one embodiment, the set of radiomic features includes 248 radiomic features extracted from tumoral and peritumoral regions of the members of the set of digitized images. In another embodiment, another, different number of radiomic features may be extracted. Extracting the set of radiomic features includes acquiring electronic data, reading from a computer file, receiving a computer file, reading from a computer memory, or other computerized activity not practically performed in the human mind.

Method 400 also includes, at 450, generating a set of discriminative features by selecting, using an mRMR approach, a threshold number of the top radiomic features that discriminate PD-L1 expression from absence of PD-L1. The set of discriminative features includes at least one tumoral radiomic feature, and at least two peritumoral radiomic features. For example, in one embodiment, the at least two peritumoral features includes a peritumoral Gabor feature (f=2, θ=3πi/8) extracted from a first 0 mm to 2 mm peritumoral annular ring, and a CoLlAGe feature extracted from a third 4 mm to 6 mm peritumoral annular ring. In this embodiment, the at least one intratumoral feature includes a Laws feature. In another embodiment, another, different feature selection technique may be employed. Generating the set of discriminative features includes acquiring electronic data, reading from a computer file, receiving a computer file, reading from a computer memory, or other computerized activity not practically performed in the human mind. In another embodiment, another, different feature selection approach may be employed.

Method 400 also includes, at 460, generating a training set. The training set includes a first subset of the set of images. The training set includes at least one image acquired of a patient that experienced recurrence, and at least one image acquired of a patient that did not experience recurrence. Generating the training set includes acquiring electronic data, reading from a computer file, receiving a computer file, reading from a computer memory, or other computerized activity not practically performed in the human mind.

Method 400 also includes, at 465, generating a testing set. The testing set includes a second, disjoint subset of the set of images. The testing set includes at least one image acquired of a patient that experienced recurrence, and at least one image acquired of a patient that did not experience recurrence. Generating the testing set includes acquiring electronic data, reading from a computer file, receiving a computer file, reading from a computer memory, or other computerized activity not practically performed in the human mind. In one embodiment, the training set includes imagery acquired of n=116 patients, and the testing set includes imagery acquired of n=50 patients. In another embodiment, the training set or the testing set may have other, different sizes.

Method 400 also includes, at 470, training the machine learning classifier to generate a probability of recurrence using the training set. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Once the machine learning classifier has been trained, it can be applied to new imaging data without repeating training, however training may optionally be repeated in order to make adjustments to the machine learning classifier given a new set of training data, for example to improve performance among images acquired with a different type of CT scanner or at a different medical institution.

Method 400 further includes, at 480, testing the machine learning classifier using the testing set. Testing the machine learning classifier includes testing the machine learning classifier using an independent validation set which is distinct from the set used for modeling the classifier. Statistical matrices, including AUC, accuracy, sensitivity, or precision may be computed to evaluate performance of the machine learning classifier on the validation set based on the outcome of interest.

In one embodiment, method 400 also includes training the machine learning classifier to generate a prognosis of OS using the training set. In another embodiment, method 400 also includes training the machine learning classifier to generate a prognosis of DFS using the training set.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 100, 200, or 300, method 400, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved prediction of recurrence may produce the technical effect of improving the administration of chemotherapy or immunotherapy, by increasing the accuracy of and decreasing the time required to determine if a patient is likely or unlikely to experience recurrence. Treatments and resources, including expensive chemotherapy agents may be more accurately tailored to patients with a likelihood of benefiting from said treatments and resources, including responding to chemotherapy, so that more appropriate treatment protocols may be employed, and expensive resources are not wasted, when CT images are more accurately and more quickly assessed for likelihood of recurrence. Controlling a recurrence prediction apparatus based on improved, more accurate analysis of CT images further improves the operation of the system, processor, or apparatus, since the accuracy of the system, processor, or apparatus is increased and unnecessary operations will not be performed. Embodiments described herein, including at least operations 100, 200, or 300, method 400, or apparatus 500 or 600, resolve features extracted from CT imagery at a higher order or higher level than a human can resolve in the human mind or with pencil and paper. For example, properties of the CT image that are not perceivable by the human eye may be detected by embodiments. Peritumoral radiomic features generated by embodiments are not properties of tumoral tissue that are perceivable by the human eye, and their computation is not practically performed in the human mind. A machine learning classifier as described herein may not be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 5:
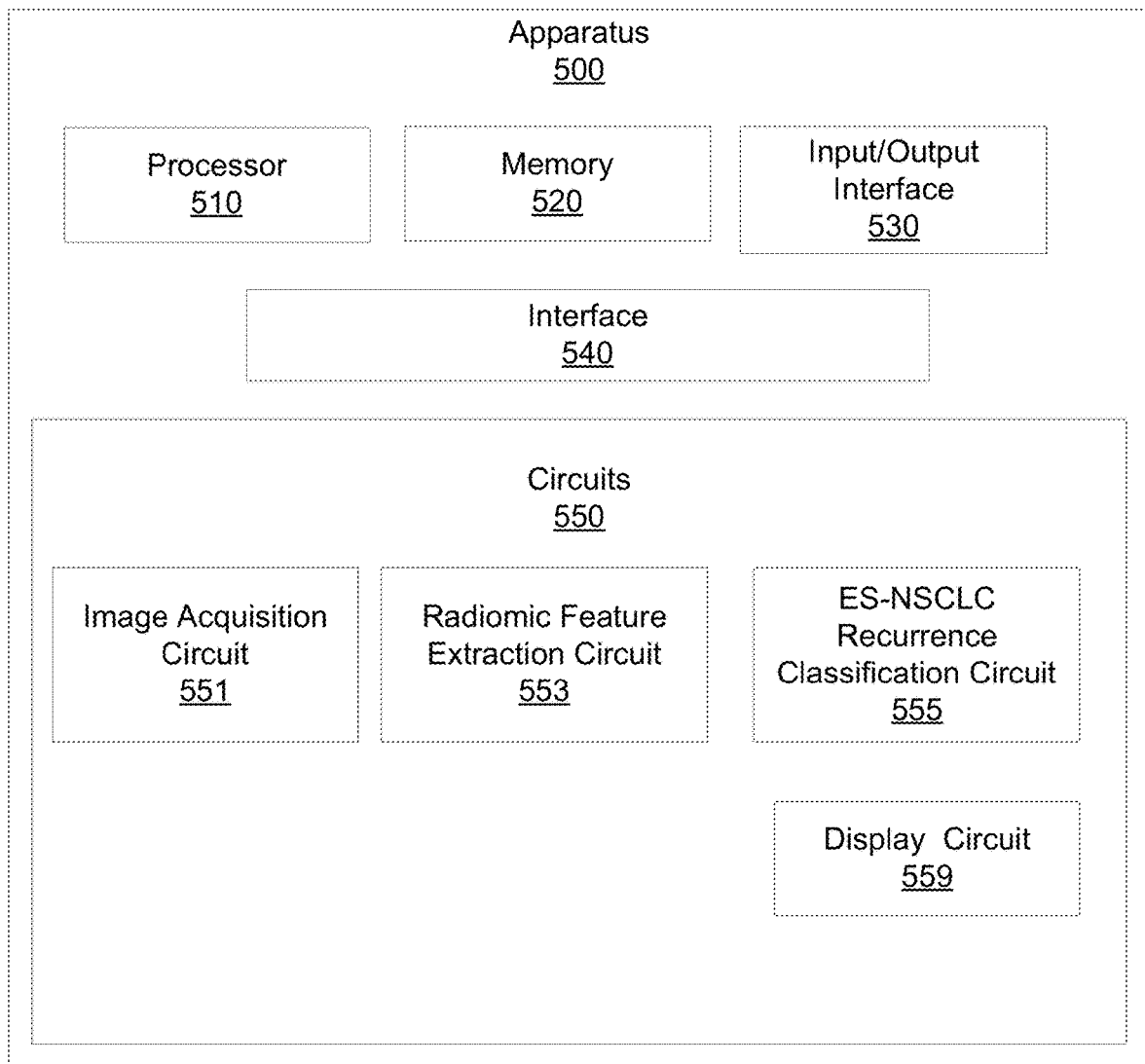
FIG. 5 illustrates an example apparatus for predicting recurrence in ES-NSCLC.

FIG. 5 illustrates an example apparatus 500. Apparatus 500 may be configured to predict recurrence in patients demonstrating ES-NSCLC. Apparatus 500 includes a processor 510. Apparatus 500 also includes a memory 520. Processor 510 may, in one embodiment, include circuitry such as, but not limited to, one or more single-core or multi-core processors. Processor 510 may include any combination of general-purpose processors and dedicated processors (e.g., graphics processors, application processors, etc.). The processors may be coupled with or may include memory (e.g. memory 520) or storage and may be configured to execute instructions stored in the memory 520 or storage to enable various apparatus, applications, or operating systems to perform the operations. Memory 520 is configured to store a radiological image of a region of tissue demonstrating ES-NSCLC. The radiological image has a plurality of pixels, a pixel having an intensity. Memory 520 may be further configured to store a training set of radiological images, or a testing set of radiological images. Memory 520 may be further configured to store metadata associated with radiological images, including PD-L1 expression data, recurrence status data, OS data, or DFS data.

Apparatus 500 also includes an input/output (I/O) interface 530, a set of circuits 550, and an interface 540 that connects the processor 510, the memory 520, the I/O interface 530, and the set of circuits 550. I/O interface 530 may be configured to transfer data between memory 520, processor 510, circuits 550, and external devices, for example, a CT system or a cancer recurrence prediction system.

The set of circuits 550 includes an image acquisition circuit 551, a radiomic feature extraction circuit 553, an ES-NSCLC recurrence classification circuit 555, and a display circuit 557. Image acquisition circuit 551 is configured to access a radiological image of a region of tissue demonstrating ES-NSCLC. The radiological image has a plurality of pixels, a pixel having an intensity. In one embodiment the radiological image is a 3D CT image of a region of tissue demonstrating ES-NSCLC. In one embodiment, the 3D CT image includes a plurality of 2D slices having a slice-thickness of between 1 mm and 5 mm respectively. In another embodiment, other types of radiological image may be accessed or employed. Accessing the radiological image may include accessing a radiological image stored in memory 520. In one embodiment, accessing the radiological image may include accessing a radiological image stored in a data storage device, including a hard disk drive, a solid state device, a tape drive, or accessing a radiological image over a local area network. Accessing the radiological image includes acquiring electronic data, reading from a computer file, receiving a computer file, reading from a computer memory, or other computerized activity not practically performed in the human mind.

Radiomic feature extraction circuit 553 is configured to extract a set of radiomic features from the radiological image. The set of radiomic features are positively correlated with programmed death-ligand 1 (PD-L1) expression. In one embodiment, the set of radiomic features includes at least two peritumoral features extracted from a peritumoral region. The peritumoral region may extend from 0 mm to 6 mm from a boundary of the tumor represented in the radiological image. The set of radiomic features also includes at least one intratumoral feature. The at least two peritumoral features includes a peritumoral Gabor feature (f=2, θ=3π/8) extracted from a first 0 mm to 2 mm peritumoral annular ring, and a CoLIAGe feature extracted from a third 4 mm to 6 mm peritumoral annular ring. The at least one intratumoral feature includes a Laws feature. In another embodiment, other radiomic features, or other numbers of radiomic features, may be extracted.

ES-NSCLC recurrence classification circuit 555 is configured to compute a probability that the region of tissue will experience ES-NSCLC recurrence. ES-NSCLC recurrence classification circuit 555 computes the probability based, at least in part, on the set of radiomic features, using a machine learning approach. ES-NSCLC recurrence classification circuit 555 is also configured to generate a classification of the region of tissue as likely to experience recurrence or non-recurrence based, at least in part, on the probability. In one embodiment, ES-NSCLC recurrence classification circuit 555 is configured as an LDA classifier. In another embodiment, ES-NSCLC recurrence classification circuit 555 is configured as another, different type of machine learning classifier, including, for example a QDA classifier, a random forest classifier, or a deep learning classifier, including a CNN.

Display circuit 557 is configured to display the classification. In one embodiment, display circuit 557 is further configured to display the classification and at least one of the probability, the set of radiomic features, or the radiological image. Displaying the classification and at least one of the probability, the set of radiomic features, or the radiological image may also include printing the classification and at least one of the probability, the set of radiomic features, or the radiological image.

Figure 6:
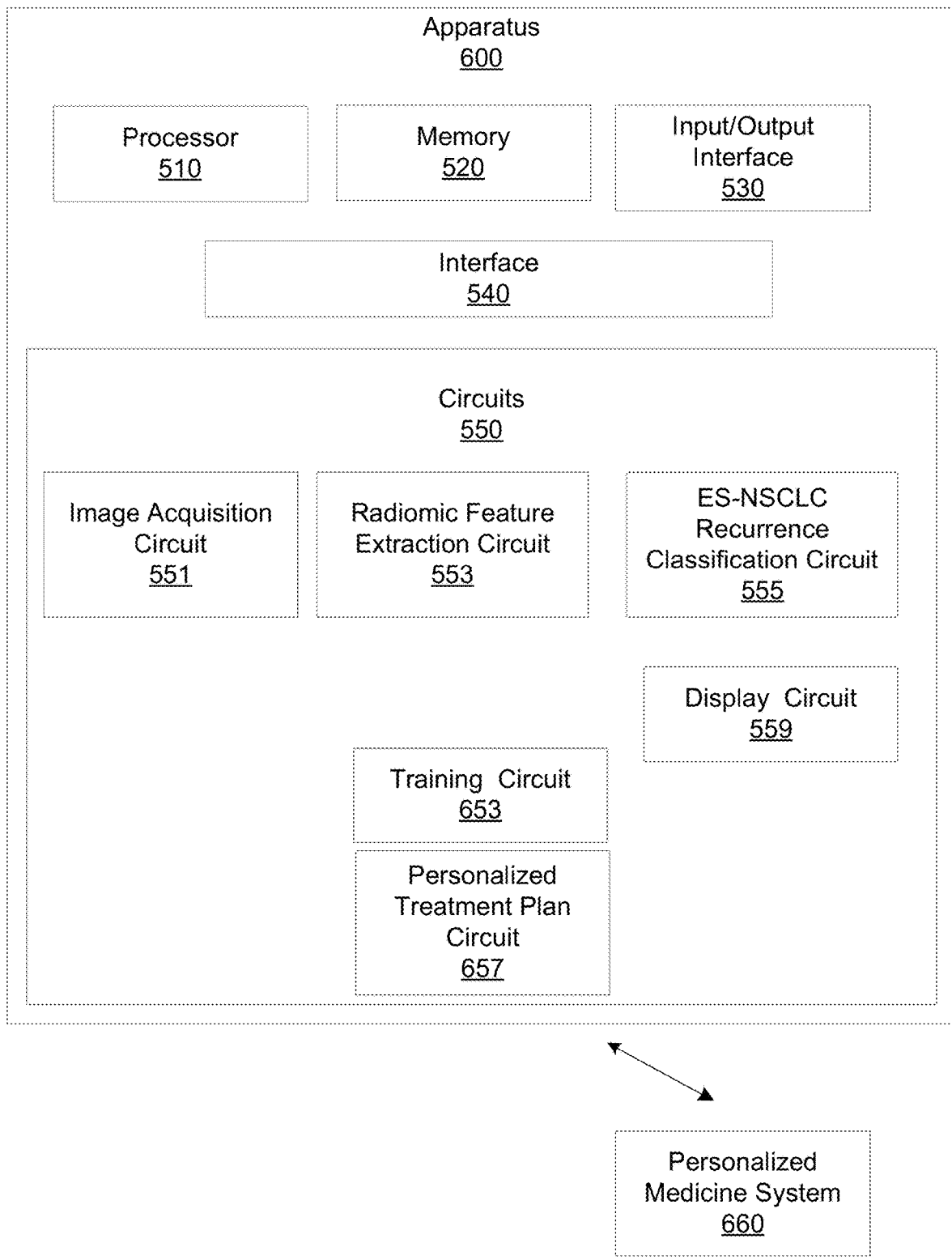
FIG. 6 illustrates an example apparatus for predicting recurrence in ES-NSCLC.

FIG. 6 illustrates an example apparatus 600 that is similar to apparatus 500 but that includes additional details and elements. In one embodiment, apparatus 600 includes a training circuit 653. Training circuit 653 may be configured to train ES-NSCLC recurrence classification circuit 555, a machine learning classifier, including a LDA, to classify a region of tissue demonstrating ES-NSCLC according to techniques described herein. In one embodiment, training circuit 653 is configured to access a set of radiological images of a ROT demonstrating ES-NSCLC pathology, where the ROT includes a tumoral region and a peritumoral region, where a digitized image includes a plurality of pixels, a pixel having an intensity. The set of digitized images includes images of patients who had curative surgery, with or without adjuvant chemotherapy, where a recurrence status, an OS time, and a DFS time for each patient, respectively, is known.

In this embodiment, training circuit 653 is also configured to access a set of tissue sections of the ROT corresponding to each member of the set of radiological images, respectively. A member of the set of tissue sections may include, for example, formalin fixed paraffin embedded (FFPE) tissue obtained from surgically resected early stage non-small cell lung cancer patients. The FFPE tissue is cut into the sections from which whole slides are created. In this embodiment, training circuit 653 is also configured to evaluate PD-L1 expression in each of the tissue sections. Training circuit 653 may be configured to evaluate PD-L1 expression in each of the tissue sections using a PD-L1 antibody approach. In another embodiment, other techniques may be employed to evaluate PD-L1 expression.

In this embodiment, training circuit 653 is also configured to extract a set of radiomic features from the set of radiological images. In one embodiment, training circuit 653 is configured to extract 248 radiomic features are extracted from each member of the set of radiological images, respectively. In another embodiment, other numbers of radiomic features may be extracted. In another embodiment, training circuit 653 is configured to receive the set of radiomic features from radiomic feature extraction circuit 553.

In this embodiment, training circuit 653 is also configured to generate a set of discriminative features by selecting a threshold number of the top radiomic features that discriminate PD-L1 expression from absence of PD-L1 from the set of radiomic features. In one embodiment, the threshold number is three. In another embodiment, the threshold number may be another, different integer, for example, four, five, ten, or other positive integer. In one embodiment, training circuit 653 is configured to use an mRMR feature selection approach to select the threshold number of the top radiomic features. In another embodiment, training circuit 653 is configured to use another, different feature selection approach. In one embodiment, the set of discriminative features includes at least one tumoral radiomic feature, and at least two peritumoral radiomic features. In another embodiment, other, different features or numbers of features may be selected.

In this embodiment, training circuit 653 is also configured to generate a training set. The training set includes a first subset of the set of radiological images. The training set includes at least one image acquired of a patient that experienced recurrence, and at least one image acquired of a patient that did not experience recurrence.

In this embodiment, training circuit 653 is also configured to generate a testing set. The testing set includes a second, disjoint subset of the set of radiological images. The testing set includes at least one image acquired of a patient that experienced recurrence, and at least one image acquired of a patient that did not experience recurrence.

In this embodiment, training circuit 653 is also configured to train the ES-NSCLC recurrence classification circuit 555 to generate a probability of recurrence using the training set. Training circuit 653 may be further configured to train ES-NSCLC recurrence classification circuit 555 to generate an OS prognosis, or a DFS prognosis.

In this embodiment, training circuit 653 is further configured to test the ES-NSCLC recurrence classification circuit 555 using the testing set.

Training circuit 653 may be configured to train ES-NSCLC recurrence classification circuit 555 or test ES-NSCLC recurrence classification circuit 555 until a threshold level of accuracy or loss is achieved, until a threshold time has been spent training the ES-NSCLC recurrence classification circuit 555, until a threshold amount of computational resources have been expended training ES-NSCLC recurrence classification circuit 555, until a user terminates training, or some combination thereof. Other training termination conditions may be employed. Once ES-NSCLC recurrence classification circuit 555 has been trained, it can be applied to new imaging data without repeating training, however training may be repeated in order to make adjustments to ES-NSCLC recurrence classification circuit 555 given a new set of training data (e.g., a different training set), for example to improve performance among images acquired with a different type of CT scanner or at a different medical institution.

Apparatus 600 also includes personalized treatment plan circuit 657. Personalized treatment plan circuit 657 is configured to generate a personalized ES-NSCLC treatment plan based, at least in part, on the classification. The personalized treatment plan circuit 657 may be further configured to generate the personalized ES-NSCLC treatment plan based the radiological image or the set of radiomic features. Personalized treatment plan circuit 657 may be configured to generate a personalized ES-NSCLC treatment plan for the patient of whom the radiological image was acquired based, at least in part, on the classification, the radiological image, or the set of radiomic features. Defining a personalized ES-NSCLC treatment plan facilitates delivering a particular treatment that will be therapeutically active to the patient, while minimizing negative or adverse effects experienced by the patient. For example, the personalized ES-NSCLC treatment plan may suggest a surgical treatment, may define an immunotherapy agent dosage or schedule, or a chemotherapy agent dosage or schedule, for a patient identified as likely to experience recurrence. For a patient classified as unlikely to experience recurrence, other treatments may be suggested.

FIG. 6 further illustrates personalized medicine device 660. Apparatus 600 may be configured to provide the classification, the radiological image, the set of radiomic features, or other data to personalized medicine device 660. Personalized medicine device 660 may be, for example, a computer assisted diagnosis (CADx) system, an ES-NSCLC recurrence prediction system, or other type of personalized medicine device that may be used to facilitate the prediction of disease recurrence. In one embodiment, personalized treatment plan circuit 657 may control personalized medicine device 660 to display the personalized ES-NSCLC treatment plan, the radiological image, or the set of radiomic features on a computer monitor, a smartphone display, a tablet display, or other displays.

Figure 7:
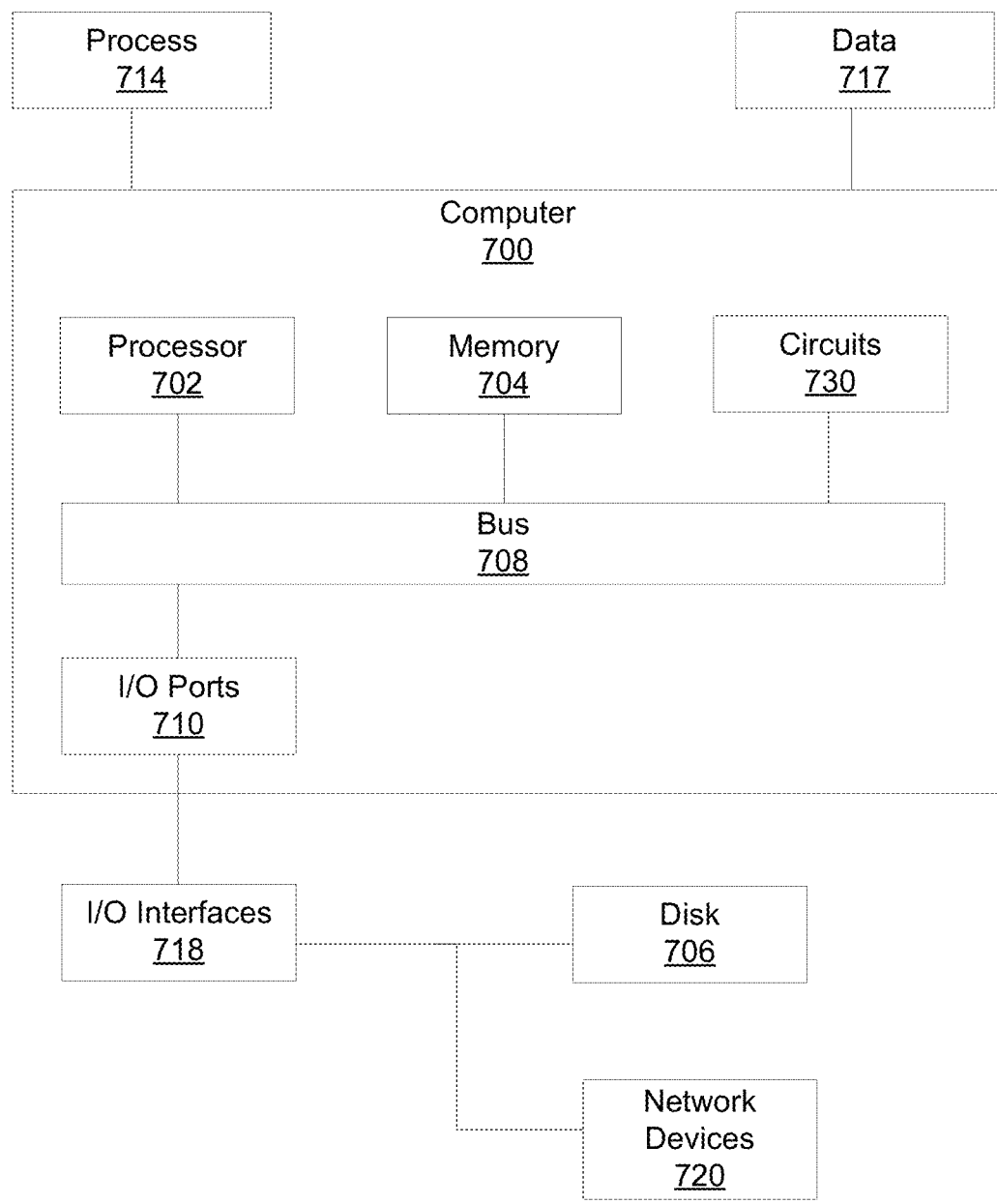
FIG. 7 illustrates an example computer in which embodiments described herein may operate.

FIG. 7 illustrates an example computer 700 in which example methods illustrated herein can operate and in which example methods, apparatus, circuits, operations, or logics may be implemented. In different examples, computer 700 may be part of an ES-NSCLC recurrence prediction system or apparatus, or a CT system, or may be operably connectable to a ES-NSCLC recurrence prediction system or apparatus, or a CT system.

Computer 700 includes a processor 702, a memory 704, and input/output (I/O) ports 710 operably connected by a bus 708. In one example, computer 700 may include a set of logics or circuits 730 that perform operations for or a method of predicting recurrence, including ES-NSCLC recurrence, using a machine learning classifier. Thus, the set of circuits 730, whether implemented in computer 700 as hardware, firmware, software, and/or a combination thereof may provide means (e.g., hardware, firmware, circuits) for performing ES-NSCLC recurrence prediction based on CT imagery of tissue demonstrating ES-NSCLC. In different examples, the set of circuits 730 may be permanently and/or removably attached to computer 700.

Processor 702 can be a variety of various processors including dual microprocessor and other multi-processor architectures. Processor 702 may be configured to perform steps of methods claimed and described herein. Memory 704 can include volatile memory and/or non-volatile memory. A disk 706 may be operably connected to computer 700 via, for example, an input/output interface (e.g., card, device) 718 and an input/output port 710. Disk 706 may include, but is not limited to, devices like a magnetic disk drive, a tape drive, a Zip drive, a flash memory card, or a memory stick. Furthermore, disk 706 may include optical drives like a CD-ROM or a digital video ROM drive (DVD ROM). Memory 704 can store processes 714 or data 717, for example. Data 717 may, in one embodiment, include CT images, DCE-MRI images, or other radiological images. Disk 706 or memory 704 can store an operating system that controls and allocates resources of computer 700.

Bus 708 can be a single internal bus interconnect architecture or other bus or mesh architectures. While a single bus is illustrated, it is to be appreciated that computer 700 may communicate with various devices, circuits, logics, and peripherals using other buses that are not illustrated (e.g., PCIE, SATA, Infiniband, 794, USB, Ethernet).

Computer 700 may interact with input/output devices via I/O interfaces 718 and input/output ports 710. Input/output devices can include, but are not limited to, CT systems, MRI systems, digital whole slide scanners, an optical microscope, a keyboard, a microphone, a pointing and selection device, cameras, video cards, displays, disk 706, network devices 720, or other devices. Input/output ports 710 can include but are not limited to, serial ports, parallel ports, or USB ports.

Computer 700 may operate in a network environment and thus may be connected to network devices 720 via I/O interfaces 718 or I/O ports 710. Through the network devices 720, computer 700 may interact with a network. Through the network, computer 700 may be logically connected to remote computers. The networks with which computer 700 may interact include, but are not limited to, a local area network (LAN), a wide area network (WAN), or other networks, including the cloud.

Examples herein can include subject matter such as an apparatus, a recurrence prediction system, including an ES-NSCLC recurrence prediction system, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting ES-NSCLC recurrence, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method comprising:
    accessing a pre-surgical digitized image of a region of tissue (ROT) demonstrating cancerous pathology for a patient having non-small cell lung cancer (NSCLC), where the pre-surgical digitized image is an image taken prior to surgery;
    extracting a set of radiomic features from the pre-surgical digitized image, wherein the set of radiomic features comprise at least one peritumoral radiomic textural feature and an intratumoral radiomic textural feature, and wherein the at least one peritumoral radiomic textural feature includes a first peritumoral feature extracted from a first peritumoral annular ring around a tumoral region of a tumor and a second peritumoral feature extracted from a second peritumoral annular ring that is around the tumoral region and outside of the first peritumoral annular ring;
    positively correlating the set of radiomic features with a programmed death-ligand 1 (PD-L1) expression;
    providing the set of radiomic features to a machine learning classifier;
    receiving, from the machine learning classifier, a probability that the ROT will experience cancer recurrence of NSCLC, where the machine learning classifier computes the probability based, at least in part, on the set of radiomic features;
    generating a classification of the ROT as likely to experience recurrence or non-recurrence of NSCLC based, at least in part, on the probability;
    generating a personalized treatment plan for the patient based upon the classification and the at least one of the probability, the personalized treatment plan comprising surgical treatment, an immunotherapy agent dosage or schedule, or a chemotherapy agent dosage or schedule; and
    administering the personalized treatment plan to the patient.

2. The method of claim 1, wherein the set of radiomic features are evaluated with an E1L3N anti-PDL1 antibody.

3. The method of claim 1, wherein the set of radiomic features are extracted from a single pre-surgical digitized image.

4. The method of claim 1, wherein the at least one peritumoral radiomic textural feature includes a peritumoral Gabor feature and a CoLIAGe feature.

5. The method of claim 1, wherein the machine learning classifier is a discriminant analysis classifier.

6. A method comprising:
    accessing a pre-surgical digitized image of a region of tissue (ROT) demonstrating cancerous pathology for a patient having non-small cell lung cancer (NSCLC), where the pre-surgical digitized image is an image taken prior to surgery;
    extracting a set of radiomic features from the pre-surgical digitized image, where the set of radiomic features includes at least two peritumoral features and at least one intratumoral feature, and where the at least two peritumoral features includes a peritumoral Gabor feature extracted from a first 0 mm to 2 mm peritumoral annular ring, and a CoLIAGe feature extracted from a third 4 mm to 6 mm peritumoral annular ring;
    positively correlating the set of radiomic features with a programmed death-ligand 1 (PD-L1) expression;
    providing the set of radiomic features to a machine learning classifier;
    receiving, from the machine learning classifier, a probability that the ROT will experience cancer recurrence of NSCLC, where the machine learning classifier computes the probability based, at least in part, on the set of radiomic features;

generating a classification of the ROT as likely to experience recurrence or non-recurrence of NSCLC based, at least in part, on the probability;
generating a personalized treatment plan for the patient based upon the classification and the at least one of the probability, the set of radiomic features, or the pre-surgical digitized image, the personalized treatment plan comprising surgical treatment, an immunotherapy agent dosage or schedule, or a chemotherapy agent dosage or schedule; and
administering the personalized treatment plan to the patient.

7. The method of claim 6, where the PD-L1 expression is positively correlated from a texture feature of the set of radiomic features.

8. The method of claim 6, where the classification of the ROT is computed using a linear discriminant analysis (LDA) machine learning approach.

9. The method of claim 6, where the at least one intratumoral feature includes a Laws feature.

10. The method of claim 6, where the pre-surgical digitized image is a three dimensional (3D) computed-tomography (CT) image of the ROT, which demonstrates early stage non-small cell lung cancer (ES-NSCLC).

11. The method of claim 10, where the 3D CT image includes a plurality of two-dimensional (2D) slices having a slice-thickness of between 1 mm and 5 mm respectively, and where the set of radiomic features are extracted from at least one of the plurality of 2D slices.

12. The method of claim 6, further comprising:
determining from the set of radiomic features a set of most discriminative radiomic features in separating presence of PD-L1 expression from its absence, wherein the set of most discriminative radiomic features comprise tumoral and peritumoral features; and
training the machine learning classifier based on the set of most discriminative radiomic features.

13. A method comprising:
accessing a pre-surgical digitized image of a region of tissue (ROT) demonstrating cancerous pathology for a patient having non-small cell lung cancer (NSCLC), where the pre-surgical digitized image is an image taken prior to surgery;
extracting a set of radiomic features from the pre-surgical digitized image, wherein the set of radiomic features comprise at least one peritumoral radiomic textural feature and an intratumoral radiomic textural feature, and wherein the at least one peritumoral radiomic textural feature includes a first peritumoral feature extracted from a first peritumoral annular ring around a tumoral region of a tumor and a second peritumoral feature extracted from a second peritumoral annular ring that is around the tumoral region and outside of the first peritumoral annular ring;
positively correlating the set of radiomic features with a programmed death-ligand 1 (PD-L1) expression;
determining from the set of radiomic features a set of most discriminative radiomic features in separating presence of PD-L1 expression from its absence; and
providing the set of radiomic features to a machine learning classifier, wherein the machine learning classifier is trained based on the set of most discriminative radiomic features;
receiving, from the machine learning classifier, a probability that the ROT will experience cancer recurrence of NSCLC, where the machine learning classifier computes the probability based, at least in part, on the set of radiomic features;
generating a classification of the ROT as likely to experience recurrence or non-recurrence of NSCLC based, at least in part, on the probability;
generating a personalized treatment plan for the patient based upon the classification and the at least one of the probability, the personalized treatment plan comprising surgical treatment, an immunotherapy agent dosage or schedule, or a chemotherapy agent dosage or schedule; and
administering the personalized treatment plan to the patient.

14. The method of claim 13, where a minimum redundancy, maximum relevance (mRMR) feature selection method is employed to select the set of most discriminative radiomic features.

15. The method of claim 13, where the set of radiomic features are extracted from a single pre-surgical digitized image.

16. The method of claim 13, further comprising:
accessing a set of tissue sections of the ROT corresponding to each member of the set of images; and
evaluating PD-L1 expression in each of the tissue sections using a PD-L1 antibody approach.

17. The method of claim 13, where the pre-surgical digitized image is a three dimensional (3D) computed-tomography (CT) image of the ROT, which demonstrates early stage non-small cell lung cancer (ES-NSCLC).

18. The method of claim 17, where the 3D CT image includes a plurality of two-dimensional (2D) slices having a slice-thickness of between 1 mm and 5 mm respectively, and where the set of radiomic features are extracted from at least one of the plurality of 2D slices.

19. The method of claim 13, where the intratumoral radiomic textural feature includes a Laws feature.

20. The method of claim 13, where the set of radiomic features includes at least two peritumoral features extracted from a peritumoral region extending 0 mm to 6 mm from a boundary of a tumor represented in the pre-surgical digitized image, and at least one intratumoral feature, where the at least two peritumoral features includes a peritumoral Gabor feature extracted from a first 0 mm to 2 mm peritumoral annular ring, and a CoLlAGe feature extracted from a third 4 mm to 6 mm peritumoral annular ring, and where the at least one intratumoral feature includes a Laws feature.

\* \* \* \* \*